United States Patent
Callcut et al.

(10) Patent No.: US 12,340,895 B2
(45) Date of Patent: Jun. 24, 2025

(54) METHOD AND SYSTEMS FOR THE AUTOMATED DETECTION OF FREE FLUID USING ARTIFICIAL INTELLIGENCE FOR THE FOCUSED ASSESSMENT SONOGRAPHY FOR TRAUMA (FAST) EXAMINATION FOR TRAUMA CARE

(71) Applicant: The Regents of the University of California, Oakland, CA (US)

(72) Inventors: Rachael Callcut, Oakland, CA (US); Michael Blum, Oakland, CA (US); Matthew O'Brien, Oakland, CA (US)

(73) Assignee: The Regents of the University of California, Oakland, CA (US)

(*) Notice: Subject to any disclaimer, the term of this patent is extended or adjusted under 35 U.S.C. 154(b) by 519 days.

(21) Appl. No.: 17/641,279

(22) PCT Filed: Sep. 18, 2020

(86) PCT No.: PCT/US2020/051392
§ 371 (c)(1),
(2) Date: Mar. 8, 2022

(87) PCT Pub. No.: WO2021/055676
PCT Pub. Date: Mar. 25, 2021

(65) Prior Publication Data
US 2022/0293243 A1   Sep. 15, 2022

Related U.S. Application Data

(60) Provisional application No. 62/902,278, filed on Sep. 18, 2019.

(51) Int. Cl.
*G16H 30/40* (2018.01)
*A61B 8/08* (2006.01)
(Continued)

(52) U.S. Cl.
CPC ............. *G16H 30/40* (2018.01); *A61B 8/085* (2013.01); *G06N 3/08* (2013.01); *G06T 7/0012* (2013.01);
(Continued)

(58) Field of Classification Search
CPC ........ G16H 30/20; G16H 15/00; G16H 40/63; G16H 40/67; G16H 30/40; G16H 50/20; G16H 50/70
(Continued)

(56) References Cited

U.S. PATENT DOCUMENTS

| | | | |
|---|---|---|---|
| 2008/0146932 A1* | 6/2008 | Chalana | A61B 8/0866 600/447 |
| 2019/0188852 A1* | 6/2019 | Reicher | G06T 7/0014 |
| 2020/0210767 A1* | 7/2020 | Do | G06T 11/008 |

OTHER PUBLICATIONS

Becker et al., (2010) "Is the FAST exam reliable in severely injured patients?," Injury, vol. 41, No. 5, pp. 479-483.
(Continued)

*Primary Examiner* — Ajibola A Akinyemi
(74) *Attorney, Agent, or Firm* — Edward J. Baba; Michael J. Blessent; Bozicevic, Field & Francis LLP

(57) ABSTRACT

Provided are systems and methods for analyzing sonograms of abdomen to identify presence or absence of free fluid in the abdomen. The systems and methods are useful for performing or assisting with point of care diagnosis of presence of internal bleeding in trauma patients without requiring input from a radiologist or another clinician trained to analyze sonograms for presence or absence of free fluid. Also provided are methods and system for training a medical imaging system for analyzing sonograms of abdomen to identify presence or absence of free fluid in the abdomen.

28 Claims, 9 Drawing Sheets

FAST Left Upper Quadrant View with Free Fluid Present

Annotation of Anatomic Structures

Original Image from Point of Care Ultrasound

(51) Int. Cl.
   *G06N 3/08*  (2023.01)
   *G06T 7/00*  (2017.01)
   *G06V 10/44*  (2022.01)
   *G06V 10/764*  (2022.01)
   *G06V 10/774*  (2022.01)
   *G06V 10/82*  (2022.01)
   *G16H 30/20*  (2018.01)

(52) U.S. Cl.
   CPC .......... *G06V 10/454* (2022.01); *G06V 10/764* (2022.01); *G06V 10/774* (2022.01); *G06V 10/82* (2022.01); *G16H 30/20* (2018.01); *G06T 2207/10132* (2013.01); *G06T 2207/20021* (2013.01); *G06T 2207/20081* (2013.01); *G06T 2207/20084* (2013.01); *G06T 2207/30004* (2013.01); *G06V 2201/031* (2022.01); *G06V 2201/10* (2022.01)

(58) Field of Classification Search
   USPC .......................................................... 382/128
   See application file for complete search history.

(56) References Cited

OTHER PUBLICATIONS

Bentley et al., (2015) "Are Live Ultrasound Models Replaceable? Traditional versus Simulated Education Module for FAST Exam," West Journal of Emergency Medicine, vol. 16, No. 6, pp. 818-822.

Blehar et al., (2015) "Learning curves in emergency ultrasound education," Academic Emergency Medicine, vol. 22, No. 5, pp. 574-582.

Brattain et al., (2018) "Machine learning for medical ultrasound: status, methods, and future opportunities," Abdominal Radiology, vol. 43, No. 4, 786-799.

Callcut et al., (2019) "The why and how our trauma patients die: A prospective Multicenter Western Trauma Association study," J. Trauma Acute Care Surg., vol. 86, No. 5, pp. 864-870.

Damewood et al., (2011) "Comparison of a multimedia simulator to a human model for teaching FAST exam image interpretation and image acquisition," The Society for Academic Emergency Medicine, vol. 18, No. 4, pp. 413-419.

Jang et al., (2012) "The technical errors of physicians learning to perform focused assessment with sonography in trauma," Academic Emergency Medicine, vol. 9, No. 1, pp. 98-101.

Krug et al., (2000) "The global burden of injuries," American Journal of Public Health, vol. 90, No. 4, pp. 523-526.

McKenney et al., (1994) "Can ultrasound replace diagnostic peritoneal lavage in the assessment of blunt trauma?," The Journal of Trauma, vol. 37, No. 3, pp. 439-441.

Melniker et al., (2006) "Randomized controlled clinical trial of point-of-care, limited ultrasonography for trauma in the emergency department: the first sonography outcomes assessment program trial," Ann. Emerg. Med., vol. 48, No. 3, pp. 227-235.

Mock et al., (2004) "Strengthening the prevention and care of injuries worldwide," The Lancet, vol. 363, No. 9427, pp. 2172-2179.

Richards et al., (2017) "Focused Assessment with Sonography in Trauma (FAST) in 2017: What Radiologists Can Learn," Radiology, vol. 283, No. 1, pp. 30-48.

Rozycki et al., (1995) "A prospective study of surgeon-performed ultrasound as the primary adjuvant modality for injured patient assessment," The Journal of Trauma and Acute Care Surgery, vol. 39, No. 3, pp. 492-498; discussion 8-500.

Sato et al., (2004) "Reevaluation of ultrasonography for solid-organ injury in blunt abdominal trauma," Journal of ultrasound in medicine : official journal of the American Institute of Ultrasound in Medicine, vol. 23, No. 12, pp. 1583-1596.

Savatmongkorngul et al., (2017) "Focused assessment with sonography for trauma: current perspectives," Open Access Emergency Medicine, vol. 9, pp. 57-62.

Sierzenski et al., (2011) "The double-line sign: a false positive finding on the Focused Assessment with Sonography for Trauma (FAST) examination," The Journal Emergency Medicine, vol. 40, No. 2, pp. 188-189.

Sjogren et al., (2016) "Image Segmentation and Machine Learning for Detection of Abdominal Free Fluid in Focused Assessment With Sonography for Trauma Examinations: A Pilot Study," J Ultrasound Med., vol. 35, No. 11, pp. 2501-2509.

Steinemann et al., (2018) "Variation in training and use of the focused assessment with sonography in trauma (FAST)," Am J Surg., vol. 215, No. 2, pp. 255-258.

Stengel et al., (2018) "Point-of-care ultrasonography for diagnosing thoracoabdominal injuries in patients with blunt trauma," Cochrane Database Systematic Reviews, vol. 12, CD012669, 129 pages.

Thomas et al., (1997) "Ultrasound evaluation of blunt abdominal trauma: program implementation, initial experience, and learning curve, The Journal of Trauma," vol. 42, No. 3, pp. 384-388; discussion 8-90.

Aman Deep et al., (2019) "Mo2047—Automated Detection of Abdominal Free Fluid in Sonography with Deep Learning", Gastroenterology, vol. 156, No. 6, May 1, 2019, pp. S-935.

Hesamian Mohammad Hesam et al., (2019) "Deep Learning Techniques for Medical Image Segmentation: Achievements and Challenges", Journal of Digital Imaging, Springer International Publishing, Cham, vol. 32, No. 4, May 29, 2019, pp. 582-596.

Keiichiro Ito et al., (2012) "Internal bleeding detection algorithm based on determination of organ boundary by low-brightness set analysis", Intelligent Robots and Systems (IROS), 2012 IEEE/RSJ International Conference On, IEEE, Oct. 7, 2012, pp. 4131-4136.

Noll Matthias et al., (2016) "An Automatic Free Fluid Detection for Morrison's-Pouch", Sep. 21, 2016, Sat 2015 18th International Conference, Austin, TX, USA, Sep. 24-27, 2015; [Lecture Notes in Computer Science; Lect. Notes Computer], Springer, Berlin, Heidelberg, pp. 77-84.

* cited by examiner

Suprapubic View Example of AI Generated Pixel Level Image
AI Generated Image

Ground Truth – Human Annotation

METHOD AND SYSTEMS FOR THE AUTOMATED DETECTION OF FREE FLUID USING ARTIFICIAL INTELLIGENCE FOR THE FOCUSED ASSESSMENT SONOGRAPHY FOR TRAUMA (FAST) EXAMINATION FOR TRAUMA CARE

CROSS-REFERENCE TO RELATED APPLICATIONS

This application is a U.S. National Stage Entry of International Application US2020/051392, filed on Sep. 18, 2020, which claims the benefit of U.S. Provisional Application Ser. No. 62/902,278, filed on Sep. 18, 2019, which application is applications are incorporated by reference herein.

STATEMENT REGARDING FEDERALLY SPONSORED RESEARCH

This invention was made with government support under grant no. K01 ES026834 awarded by The National Institutes of Health. The government has certain rights in the invention.

INTRODUCTION

Injury is the primary cause of death in young adults (1), and as a consequence, is one of the leading causes of loss of human potential (2). The majority of early preventable deaths related to injury are due to uncontrolled hemorrhage, and therefore rapid identification of hemorrhage is pivotal in mitigating the morbidity and mortality of injury (3). The Focused Assessment with Sonography for Trauma (FAST) examination has successfully functioned as a screening evaluation to improve time to intervention for injured patients with intraabdominal hemorrhage (4). The FAST examination was adopted in the 1990s to replace invasive methods such diagnostic peritoneal lavage, for patients with concern for intraabdominal hemorrhage from blunt injury, and was subsequently found to improve outcomes for injured patients (5).

The variable test characteristics of the FAST examination can be attributable to operator expertise (6, 7). When initially described in 1995 (8), the FAST examination reportedly had a sensitivity and specificity for the detection of intraabdominal injury exceeding 95%. However, a systematic review published in 2018 of the FAST examination performed in a total of 8635 patients with blunt injury, reported sensitivity and specificity for detection of intraabdominal injury to be 0.68 (95% CI 0.59 to 0.75) and 0.95 (95% CI 0.92 to 0.97), respectively (6). This large difference in test characteristics and wide confidence intervals exemplify the variable test characteristics of the FAST examination. Previous reports have demonstrated that highly trained and experienced FAST operators have improved test characteristics over novices(9, 10). Investigators have sought methods to improve operator training for over two decades (11, 12), however variability related to operator expertise still exists (13).

Machine learning, is a method of data analysis that can learn from large amounts of data, identifies patterns, and assigns probability with little human input. Deep learning is a subtype of machine learning in which data can be extracted in non-linear methods, and these methodologies have already shown to be a promising for ultrasound diagnostics, improving ultrasound based clinical workflows and disease diagnosis in non-emergency settings (14). However, there has been less focus on emergency applications in which a model could alter care in real-time.

The present disclosure addresses these as well as other needs.

SUMMARY

Provided are systems and methods for analyzing sonograms of abdomen to identify presence or absence of free fluid in the abdomen. The systems and methods are useful for performing or assisting with point of care diagnosis of presence of internal bleeding in trauma patients without requiring input from a radiologist or another clinician trained to analyze sonograms for presence or absence of free fluid. Also provided are methods and system for training a medical imaging system for analyzing sonograms of abdomen to identify presence or absence of free fluid in the abdomen.

DETAILED DESCRIPTION

Figure 1:
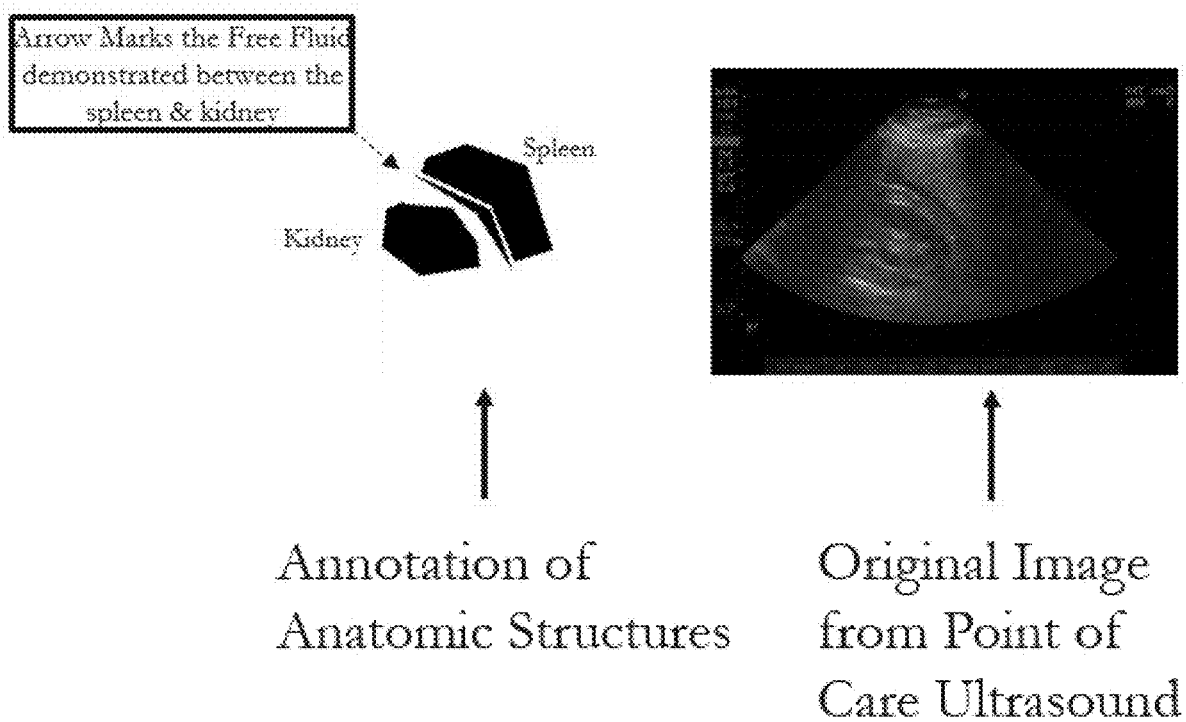
FIG. 1. Original Left Upper Quadrant FAST image and pixel level annotation. Legend: A—panel is annotated image, B—native FAST image; *: kidney, !: free fluid, #: spleen.

Provided are systems and methods for analyzing sonograms of abdomen to identify presence or absence of free fluid in the abdomen. The systems and methods are useful for performing or assisting with point of care diagnosis of presence of internal bleeding in trauma patients without requiring input from a radiologist or another clinician trained to analyze sonograms for presence or absence of free fluid. Also provided are methods and system for training a medical imaging system for analyzing sonograms of abdomen to identify presence or absence of free fluid in the abdomen. Also provided are non-transitory computer-readable media that find use, e.g., in practicing the methods of the present disclosure.

Before the methods, computer-readable media, and systems of the present disclosure are described in greater detail, it is to be understood that the methods, computer-readable media, and systems are not limited to particular embodiments described, as such may, of course, vary. It is also to be understood that the terminology used herein is for the purpose of describing particular embodiments only, and is not intended to be limiting, since the scope of the methods, computer-readable media, and systems will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the methods, computer-readable media, and systems. The upper and lower limits of these smaller ranges may independently be included in the smaller ranges and are also encompassed within the methods, computer-readable media, and systems, subject to any specifically excluded limit in the stated range. Where the stated range includes one or both of the limits, ranges excluding either or both of those included limits are also included in the methods, computer-readable media, and systems.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which the methods, computer-readable media, and systems belong. Although any methods, computer-readable media, and systems similar or equivalent to those described herein can also be used in the practice or testing of the methods, computer-readable media, and systems, representative illustrative methods, computer-readable media, and systems are now described.

All publications and patents cited in this specification are herein incorporated by reference as if each individual publication or patent were specifically and individually indicated to be incorporated by reference and are incorporated herein by reference to disclose and describe the materials and/or methods in connection with which the publications are cited. The citation of any publication is for its disclosure prior to the filing date and should not be construed as an admission that the present methods, computer-readable media, and systems are not entitled to antedate such publication, as the date of publication provided may be different from the actual publication date which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the methods, computer-readable media, and systems, which are, for clarity, described in the context of separate embodiments, may also be provided in combination in a single embodiment. Conversely, various features of the methods, computer-readable media, and systems, which are, for brevity, described in the context of a single embodiment, may also be provided separately or in any suitable sub-combination. All combinations of the embodiments are specifically embraced by the present disclosure and are disclosed herein just as if each and every combination was individually and explicitly disclosed, to the extent that such combinations embrace operable processes and/or compositions. In addition, all sub-combinations listed in the embodiments describing such variables are also specifically embraced by the present methods, computer-readable media, and systems and are disclosed herein just as if each and every such sub-combination was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present methods, computer-readable media, and systems. Any recited method can be carried out in the order of events recited or in any other order that is logically possible.

Systems and Computer-Readable Media

Aspects of the present disclosure further include systems and computer-readable media (CRM) that find use in practicing the methods disclosed herein such as for automatically identifying presence or absence of internal bleeding based on analysis of a raw sonogram. The computer-readable media and systems may be employed, e.g., to carry out any of the methods of the present disclosure or hereinbelow in the Experimental section.

One aspect of the present disclosure includes a system for analyzing a sonogram of a patient's abdomen to automatically identify anatomical structures and determine presence or absence of free fluid in the patient's abdomen.

Another aspect of the present disclosure includes a machine learning system trained for analyzing a sonogram of a patient's abdomen to automatically identify anatomical structures and determine presence or absence of free fluid in the patient's abdomen.

As used herein, the term "machine learning" is used to refer to the various classes of artificial intelligence algorithms and algorithm-driven approaches that are capable of performing machine-driven (e.g., computer-aided) identification of trained structures, with the term "deep learning" referring to a multiple-level operation of such machine learning algorithms using multiple levels of representation and abstraction. However, it will be apparent that the role of the machine learning algorithms that are applied, used, and configured in the presently described systems and methods may be supplemented or substituted by any number of other algorithm-based approaches, including variations of artificial neural networks, learning-capable algorithms, trainable object classifications, and other artificial intelligence processing techniques.

In certain embodiments, a system for analyzing a sonogram of a patient's abdomen to automatically identify anatomical structures and determine presence or absence of free fluid in the patient's abdomen may include software instructions; a processor configured to execute the software instructions; and an output. The processor may be configured to execute the software instructions for: analyzing pixels in the sonogram as representing an anatomical structure, producing a drawing of the anatomical structure based on the analyzing of the pixels; and if present, a drawing of free fluid in the patient's abdomen; and an output configured for providing: an image showing the drawing of the anatomical structure and, if present, the drawing of free fluid, and/or an indication of presence or absence of free fluid in the patient's abdomen.

The system may be embodied on a computer network, on site, e.g., on a computer terminal at a hospital where the sonograms are obtained or off-site, e.g., on a remote server or a cloud-based computing system.

In certain embodiments, the sonogram is a low-resolution sonogram obtained using a portable ultrasound machine. Thus, in certain embodiments, the systems, CRM, and methods provided herein are utilized at a point-of-care facility to efficiently provide a diagnosis or provide an annotated image of the low-resolution sonogram to assist in a diagnosis, effectively decreasing the time for medical intervention for patients suffering from internal bleeding in the abdomen. Whilst the embodiments described herein improve patient outcome when using low-resolution sonogram in an emergency setting, the systems, CRM, and methods can equally be utilized in analysis of a high-resolution sonogram obtained by, e.g., using a high resolution ultrasound machine.

In certain embodiments, the analyzing the pixels in the sonogram for carrying out image segmentation may include identifying right upper quadrant, the left upper quadrant and/or the suprapubic view of the abdomen imaged in the sonogram. In certain embodiments, all three views of the abdomen are analyzed.

In certain embodiments, the analysis may be performed in a short time frame, for example, a time frame shorter than the time required by a radiologist to analyze the sonogram. In certain embodiments, the analysis may be performed under 10 minutes, under 5 minutes, under 4 minutes, under 3 minutes, under 2 minutes, or under one minute of the system receiving a sonogram. In certain embodiments, the analysis may be performed on multiple sonograms of the abdomen of the patient. In certain embodiments, the analysis may be performed on up to 20, up to 10, or up to 5 sonograms of the abdomen of the patient.

In certain embodiments, the software instructions executed by the processor may be obtained by training a sonogram analysis system to analyze pixels of a sonogram using pre-annotated abdominal sonograms where the pixels are labeled as corresponding to anatomic structures and if present, to free fluid.

In certain embodiments, the pre-annotated abdominal sonograms comprise pixel level annotation that delineates bladder, kidney, liver, spleen, and/or free fluid. In certain embodiments, the pre-annotated abdominal sonograms are annotated by a radiologist or another trained clinician. For example, the annotation may include correlating pixels in the abdominal sonograms to anatomical structure and drawing out the anatomical structure and, optionally, labeling the drawing to indicate the name of the anatomical structure. The annotation may include correlating pixels in the abdominal sonograms to presence of free fluid indicative of hemoperitoneum.

In certain embodiments, the pre-annotated abdominal sonograms may include at least about 100 sonograms or at least about 500 sonograms, e.g., 100-500 sonograms, 200-500 sonograms, 300-500 sonograms, or 200-300 sonograms.

In certain embodiments, the training includes up to 25 repetitions or up to 50 repetitions e.g., 25-50 repetitions, 30-50 repetitions, or 40-50 repetitions with each of the pre-annotated sonogram. For example, the training may involve training the sonogram analysis system on 100-500 low-resolutions sonograms with 40-50 repetitions.

In certain embodiments, the training is performed on a UNET CNN algorithm architecture or a similar algorithm architecture. In certain embodiments, the training includes stochastic gradient descent with restarts (SGDR).

In certain embodiments, the system identifies abdominal free fluid and anatomic structures with a 71-98% accuracy depending upon the structure and quality of the image.

The system may also include an image receiving unit, an image storage unit, and an output. The output may include a screen for showing an image of the drawing of the anatomical structures and, if present, the drawing of free fluid. The output may in addition or alternatively provide an indication of presence or absence of free fluid in the patient's abdomen. In addition to a screen or a monitor, the output may be a speaker, a printer, or the like. In certain embodiments, the system may store the unannotated sonogram and a processed version of the sonogram containing drawings of anatomical structures and if present, drawing of free fluid.

A system according to embodiments of the present disclosure, may include an ultrasound machine for acquisition of one or more sonograms of the abdomen of a trauma patient suspected of having internal bleeding. The ultrasound machine may be in communication (e.g. wired or wireless communication) with the system to provide the sonograms to the system. Processing unit of the system may include the software instructions that cause the processing unit to analyze the sonograms for identification of anatomical structures and structures indicative of free abdominal fluid, which analyzed sonograms may optionally be stored in storage device and optionally displayed at image display unit. The processing unit can consist of one or more different physical computers and/or cloud-based computing system.

The analyzed sonograms may be stored in storage device along with the raw data (e.g. unannotated sonograms), for later display at the workstation, and/or for forwarding to an external display device, for example using DICOM (Digital Imaging and Communications in Medicine) interface. The term "raw image," "raw sonogram," or "unannotated sonogram" refers to the original image before any additional processing has been applied on it.

The drawing of a raw sonogram outputted by the system of the present disclosure may be a high contrast, e.g., black and white, drawing showing the anatomical structures and free fluid in a darker shade as compared to the other features of the abdomen or vice versa. The drawings of anatomical structures and free fluid may include margins that are depicted with linear or non-linear outlines. The outlines may be filled in one color (e.g., black) to delineate the anatomical structures and free fluid while the background may be indicated in another color (e.g., white).

The systems disclosed herein may, in some embodiments, include a processor-based device suitable for implementing various functionality described herein. Although not required, some portion of the implementations will be described in the general context of processor-executable instructions or logic, such as program application modules, objects, or macros being executed by one or more processors. Those skilled in the relevant art will appreciate that the described implementations, as well as other implementations, can be practiced with various processor-based system configurations, including handheld devices, such as smartphones and tablet computers, wearable devices, multiprocessor systems, microprocessor-based or programmable consumer electronics, personal computers ("PCs"), network PCs, minicomputers, mainframe computers, and the like.

The processor-based device may include one or more processors, a system memory and a system bus that couples various system components including the system memory to the processor(s). The processor-based device will at times be referred to in the singular herein, but this is not intended to limit the implementations to a single system, since in certain implementations, there will be more than one system or other networked computing device involved. Non-limiting examples of commercially available systems include, but are not limited to, ARM processors from a variety of manufactures, Core microprocessors from Intel Corporation, U.S.A., PowerPC microprocessor from IBM, Sparc microprocessors from Sun Microsystems, Inc., PA-RISC series microprocessors from Hewlett-Packard Company, 68xxx series microprocessors from Motorola Corporation.

The processor(s) may be any logic processing unit, such as one or more central processing units (CPUs), microprocessors, digital signal processors (DSPs), application-specific integrated circuits (ASICs), field programmable gate arrays (FPGAs), etc.

The system bus can employ any known bus structures or architectures, including a memory bus with memory controller, a peripheral bus, and a local bus. The system memory includes read-only memory ("ROM") and random access memory ("RAM"). A basic input/output system ("BIOS"), which can form part of the ROM, contains basic routines that help transfer information between elements within processor-based device, such as during start-up. Some implementations may employ separate buses for data, instructions and power.

The processor-based device may also include one or more solid state memories, for instance flash memory or a solid state drive (SSD), which provides nonvolatile storage of computer-readable instructions, data structures, program modules and other data for the processor-based device. The processor-based device can employ other non-transitory computer- or processor-readable media, for example a hard disk drive, an optical disk drive, or memory card media drive.

Program modules can be stored in the system memory, such as an operating system, one or more application programs, other programs or modules, drivers and program data.

The application programs may, for example, include panning/scrolling. Such panning/scrolling logic may include, but is not limited to logic that determines when and/or where a pointer (e.g., finger, stylus, cursor) enters a user interface element that includes a region having a central portion and at least one margin. Such panning/scrolling logic may include, but is not limited to logic that determines a direction and a rate at which at least one element of the user interface element should appear to move, and causes updating of a display to cause the at least one element to appear to move in the determined direction at the determined rate. The panning/scrolling logic may, for example, be stored as one or more executable instructions. The panning/scrolling logic may include processor and/or machine executable logic or instructions to generate user interface objects using data that characterizes movement of a pointer, for example data from a touch-sensitive display or from a computer mouse or trackball, or other user interface device.

The system memory may also include communications programs, for example a server and/or a Web client or browser for permitting the processor-based device to access and exchange data with other systems such as user computing systems, Web sites on the Internet, corporate intranets, or other networks as described below. The communications programs in the depicted implementation is markup language based, such as Hypertext Markup Language (HTML), Extensible Markup Language (XML) or Wireless Markup Language (WML), and operates with markup languages that use syntactically delimited characters added to the data of a document to represent the structure of the document. A number of servers and/or Web clients or browsers are commercially available such as those from Mozilla Corporation of California and Microsoft of Washington.

The operating system, application programs, other programs/modules, drivers, program data and server and/or communications programs (e.g., browser) can be stored on any of a large variety of non-transitory processor-readable media (e.g., hard disk drive, optical disk drive, SSD and/or flash memory).

A user can enter commands and information via a pointer, for example through input devices such as a touch screen via a finger, stylus, or via a computer mouse or trackball which controls a cursor. Other input devices can include a microphone, joystick, game pad, tablet, scanner, biometric scanning device, etc. These and other input devices (i.e., "I/O devices") are connected to the processor(s) through an interface such as touch-screen controller and/or a universal serial bus ("USB") interface that couples user input to the system bus, although other interfaces such as a parallel port, a game port or a wireless interface or a serial port may be used. The touch screen can be coupled to the system bus via a video interface, such as a video adapter to receive image data or image information for display via the touch screen. The processor-based device can include other output devices, such as speakers, etc.

The processor-based device may operate in a networked environment using one or more of the logical connections to communicate with one or more remote computers, servers and/or devices via one or more communications channels. These logical connections may facilitate any known method of permitting computers to communicate, such as through one or more LANs and/or WANs, such as the Internet, and/or cellular communications networks. Such networking environments are well known in wired and wireless enterprise-wide computer networks, intranets, extranets, the Internet, and other types of communication networks including telecommunications networks, cellular networks, paging networks, and other mobile networks.

When used in a networking environment, the processor-based device may include one or more wired or wireless communications interfaces (e.g., cellular radios, WI-FI radios, Bluetooth radios) for establishing communications over the network, for instance the Internet or cellular network.

In a networked environment, program modules, application programs, or data, or portions thereof, can be stored in a server computing system. Those skilled in the relevant art will recognize that these network connections are only some examples of ways of establishing communications between computers, and other connections may be used, including wirelessly.

One or more of the above-described components may be directly coupled to other components, or may be coupled to each other, via intermediary components. In some implementations, system bus is omitted and the components are coupled directly to each other using suitable connections.

Figure 8:
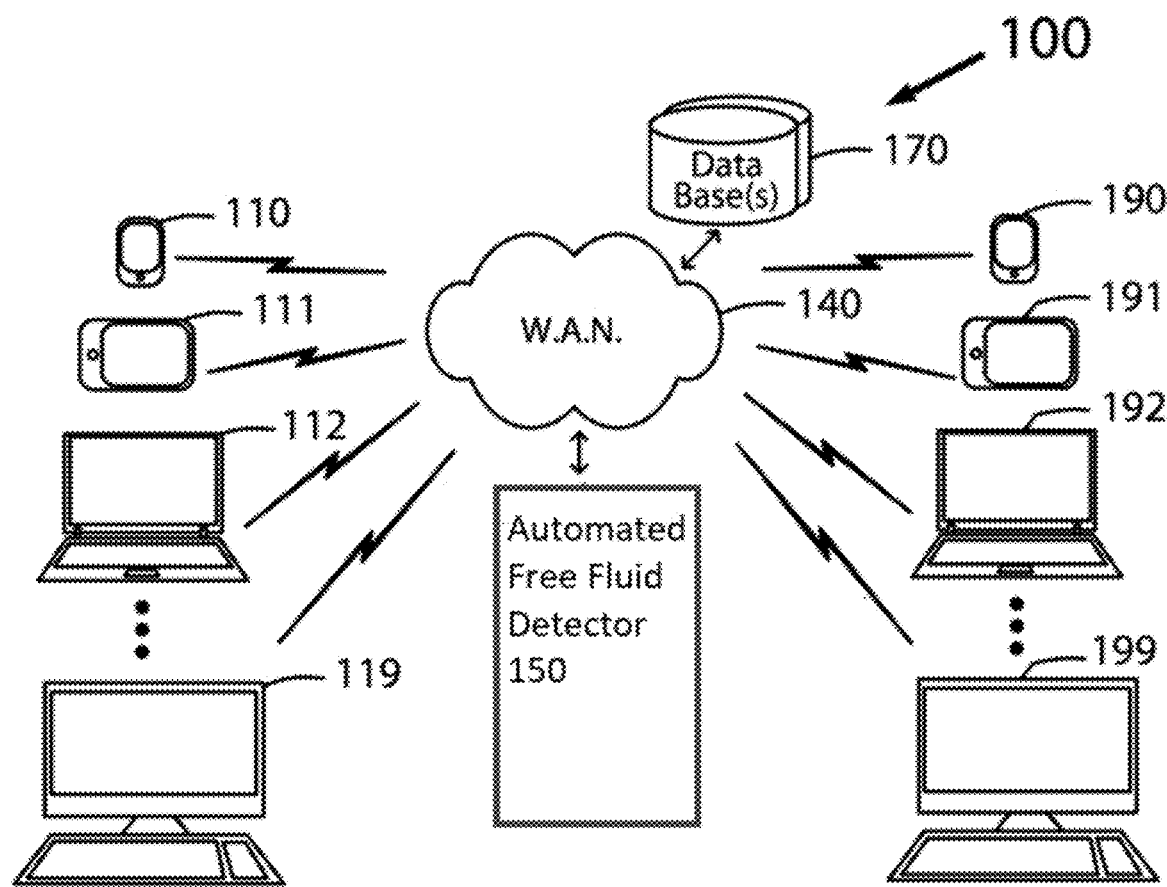
FIG. 8. Illustration of an automated free fluid detector 150 of the present disclosure communicably connected to a network of additional devices for communication, data processing, and/or inputting or outputting of images and reports.
Figure 9:
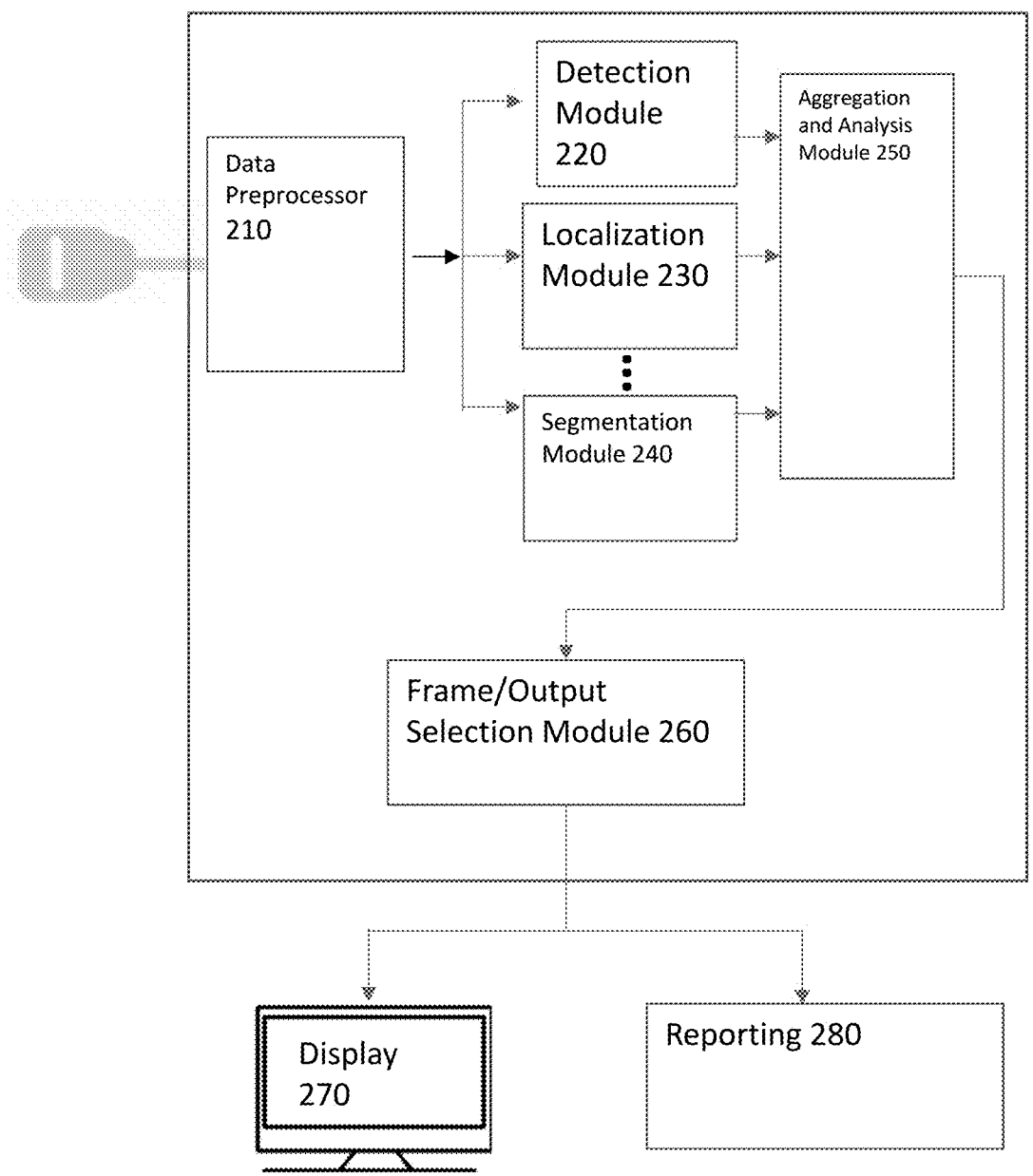
FIG. 9. An exemplary embodiment of an automated free fluid detector 150 with modules for performing various steps for analyzing a sonogram is depicted. Automated free fluid detector 150 may include or may be in communication with a display and/or reporting module.
Figure 10:
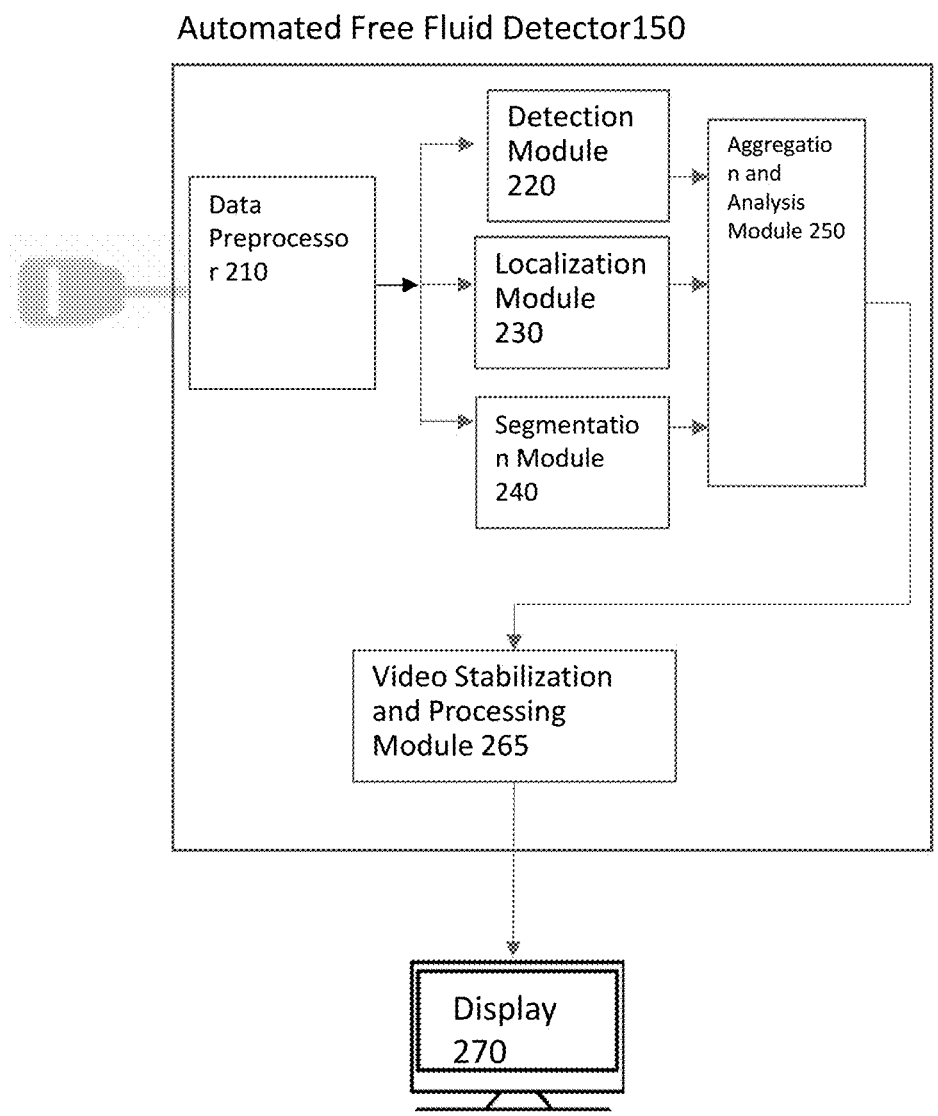
FIG. 10. An exemplary embodiment of an automated free fluid detector 150 with modules for performing various steps for analyzing a sonogram is depicted. Automated free fluid detector 150 may include or may be in communication with a display and/or reporting module. Instead of or in addition to the Frame/Output Selection Module 260 depicted in FIG. 9, the automated free fluid detector 150 may include a Video Stabilization and Processing Module 265.

Examples of modules that may be used to perform the methods disclosed herein are depicted in FIGS. 8-10. FIG. 8 depicts a system 100 comprising an automated free fluid detector 150 in communication with a wide area network (W.A.N.) module 140 which is connected to various input/output devices, such as, smartphone 110/190, tablet/iPad 111/191, laptop 112/192, monitor/desktop 119, 199 any of which may be used to provide a raw sonogram to the automated free fluid detector 150 and to output an image and/or report generated by the automated free fluid detector 150.

FIG. 9 depicts an exemplary embodiment of the automated free fluid detector 150. Data Preprocessor 210 prepares data received from an ultrasound system for automated analysis. Data preparation steps can include, but are not limited to, video and image format conversion, noise detection, image quality detection, view identification, and frame extraction. Detection Module 220 performs detection of objects of interest in image/video data, including but not limited to, anatomical structures and free fluid. Localization Module 230 performs localization of objects of interest in image/video data by placing bounding boxes around them, including but not limited to, anatomical structures and free fluid. Segmentation Module 240 performs segmentation of objects of interest in image/video data by placing bounding boxes around them, including but not limited to, anatomical structures and free fluid. Segmentation labels individual pixels in an image according to what object or objects are detected at that location. Additional processing and feature detection algorithms may be applied in parallel to Modules 220, 230 and 240. Aggregation and Analysis Module 250, outputs of analysis and feature detection modules (220, 230, 240, and others) are combined and computed upon to optimize the utility of the subsequent output. Signal strength, image quality, statistical significance and other analyses may be applied at this point. Frame/Output Selection Module 260, based on the output of Module 250, specific results and output images are selected and exported for reporting and display. Output images may contain one or more raw images along with annotations or image masks depicting relevant features, including but not limited to, anatomical structures and free fluid.

FIG. 10 depicts another embodiment of the automated free fluid detector 150. All modules are same as those described for FIG. 9 except video Stabilization and Processing Module 265, based on the output of Module 250, output video is constructed for real-time or recorded display. Output video may contain raw video along with annotations or image masks depicting relevant features, including but not limited to, anatomical structures and free fluid. This step performs the video stabilization and mapping of results to raw video that enable the presentation of (possibly sampled) frame-level analytical results in video format for display purposes.

In some embodiments provided is a non-transitory computer-readable medium (CRM) storing instructions that, when executed by a computer system, which may be a physical computer or a cloud-based computing system, cause the computer system to perform the steps of analyzing pixels in the sonograph, producing a drawing of the anatomical structure based on the analyzing of the pixels, if present, drawing an outline of free fluid in the patient's abdomen; and providing an image showing the drawing of the anatomical structure and, if present, the drawing of free fluid, and/or an indication presence or absence of free fluid in the patient's abdomen of the present disclosure, which for the sake of brevity are not reiterated herein.

In certain aspects, instructions in accordance with the computer systems described herein can be coded onto a non-transitory computer-readable medium in the form of "programming", where the term "computer-readable medium" as used herein refers to any storage or transmission medium that participates in providing instructions and/or data to a computing device for execution and/or processing. Examples of storage media include a floppy disk, hard disk, optical disk, magneto-optical disk, CD-ROM, CD-R, magnetic tape, non-volatile memory card, ROM, DVD-ROM, Blue-ray disk, solid state disk, and network attached storage (NAS), whether or not such devices are internal or external to the system. A file containing information can be "stored" on computer readable medium, where "storing" means recording information such that it is accessible and retrievable at a later date by a computer or a network. In some embodiments, the non-transitory computer-readable medium is (or is included in) a remote server, and the instructions are downloadable from the server to a computer system.

The instructions may be in the form of programming that is written in one or more of any number of computer programming languages. Such languages include, for example, Python, Pytorch, Java (Sun Microsystems, Inc., Santa Clara, CA), Visual Basic (Microsoft Corp., Redmond, WA), and C++ (AT&T Corp., Bedminster, NJ), as well as many others.

In certain embodiments, the instructions comprise non-linear deep learning algorithm, such as, a convolutional neural network trained to perform image segmentation of a sonogram to identify anatomical structures in the sonogram. In certain aspects, the present disclosure provides a machine learning system trained to perform the methods described herein. In certain embodiments, the machine learning system includes a non-transitory processor-readable storage medium that stores a processor-executable instruction; and a processor communicably coupled to the non-transitory processor-readable storage medium. The processor receives learning data comprising a plurality of unannotated sonograms and annotated versions thereof, each sonogram comprising pixels representative of an anatomical structure and of free fluid, if present, and each annotated sonogram comprising identification of an anatomical structure depicted by the pixels and of free fluid, if present; trains a convolutional neural network (CNN) model to segment anatomical structures and free fluid, if present, utilizing the received learning data; and stores the trained CNN model in the non-transitory processor-readable storage medium of the machine learning system, where the sonograms are sonograms of abdomen of patients. The trained model may be stored on servers as part of a cloud service.

In certain embodiments, the unannotated sonogram and the annotated version thereof are in a single image comprising pixels and metadata associated with the pixels, where the metadata comprises the annotation regarding pixels representative of an anatomical structure and of free fluid, if present. In certain embodiments, the metadata includes annotation regarding pixels representative of an anatomical structure and of free fluid, if present, drawings of anatomical structures and of free fluid, if present, and a label identifying each of the drawings as a particular anatomical structure and free fluid. In certain embodiments, the unannotated sonogram and the annotated version thereof are separate images. In certain embodiments, the unannotated sonogram and the annotated version thereof are in a single image in different layers. In certain embodiments, the annotated version of the sonogram is marked with the anatomical structures drawn and connected to a look up table identifying each of the anatomical structures.

In certain embodiments, the annotated sonograms used for training the CNN are produced by a radiologist or a clinician trained for annotating abdominal sonograms.

In certain embodiments, at least 10%, at least 20%, at least 30%, or at least 40% of the training sonograms comprise sonograms of patients with free fluid in the abdomen.

In certain embodiments, the processor trains a UNET CNN algorithm. In certain embodiments, the processor trains the CNN using stochastic gradient descent with restarts (SGDR).

In certain embodiments, the sonograms comprise views of right upper quadrant, RUQ, left upper quadrant, LUQ, and suprapubic, SP views and can thus train the CNN to analyze various views of an abdomen as captured by an ultrasound machine.

A non-transitory processor-readable storage medium that stores the processor-executable software instructions that include a trained CNN for analyzing abdominal sonograms, which CNN is trained as disclosed above, is also encompassed by the present disclosure.

Methods

In another aspect, a computer-implemented method for analyzing a sonogram of a patient's abdomen to automatically identify anatomical structures and determine presence or absence of free fluid in the patient's abdomen is disclosed. The method includes analyzing pixels in the sonogram as representing an anatomical structure, producing a drawing of the anatomical structure based on the analyzing of the pixels; and if present, a drawing marking the presence and extent of free fluid in the patient's abdomen; and outputting an image showing the drawing of the anatomical structure and, if present, the drawing of free fluid, and/or an indication of presence or absence of free fluid.

As noted in the context of the systems of the present disclosure, the sonogram may be a low-resolution sonogram obtained using a portable ultrasound machine although high-resolution sonograms can also be analyzed by the presently disclosed systems, CRM, and methods.

In certain embodiments, analyzing the pixels in the sonograph may include identifying right upper quadrant, the left upper quadrant and/or the suprapubic view in the sonogram prior to or in conjunction with identifying pixels corresponding to anatomical structure and to free fluid, when free fluid is present.

As noted in the context of the systems of the present disclosure, the software instructions are obtained by training a sonogram analysis system to analyze pixels of a sonogram using pre-annotated abdominal sonograms where the pixels are labeled as corresponding to anatomic structures and to free fluid. In certain embodiments, the pre-annotated abdominal sonograms comprise pixel level annotation to delineate bladder, kidney, liver, spleen, and/or free fluid. In certain embodiments, the pre-annotated abdominal sonograms are annotated by a radiologist or a similarly trained clinician. The pre-annotated abdominal sonograms may include at least about 100 sonograms, at least about 200 sonograms, at least about 300 sonograms, at least about 400 sonograms, at least about 500 sonograms. In certain embodiments, the training may involve multiple epochs, e.g., up to 25 repetitions, up to 30 repetitions, up to 40 repetitions, or up to 50 repetitions with each of the pre-annotated sonogram. In certain embodiments, the training may be performed on a UNET CNN algorithm or a similar algorithm for image segmentation. In certain embodiments, the training includes stochastic gradient descent with restarts (SGDR) to improve rate of learning.

Utility

Figure 7:
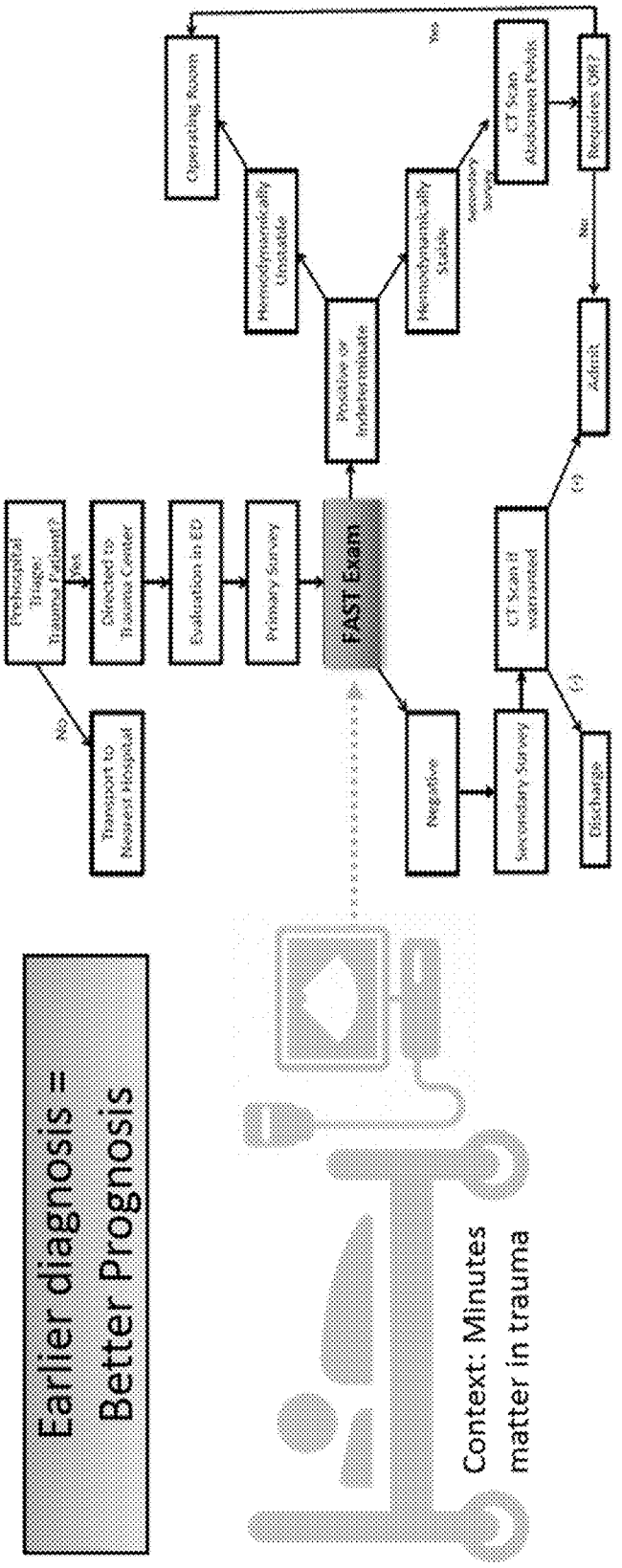
FIG. 7. Illustration of diagnosis and prognosis of a trauma patient assisted by automated and semi-automated systems.

The diagnostic accuracy of current FAST exams is moderate and inconsistent. As illustrated by the data provided herein, FAST exams can be successfully automated with increased accuracy with a decreased time frame thereby supporting timely decision making as outlined in FIG. 7.

Examples of Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure numbered 1-47 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

1. A system for analyzing a sonogram of a patient's abdomen to automatically identify anatomical structures and determine presence or absence of free fluid in the patient's abdomen, the system comprising:
    (i) software instructions;
    (ii) a processor configured to execute the instructions for:
        analyzing pixels in the sonograph as representing an anatomical structure,
        producing a drawing of the anatomical structure based on the analyzing of the pixels; and
        if present, drawing of free fluid in the patient's abdomen; and
    (iii) an output configured for providing:
        an image showing the drawing of the anatomical structure and, if present, the free fluid, and/or
        an indication presence or absence of free fluid in the patient's abdomen.

2. The system of aspect 1, wherein the sonogram is a low-resolution sonogram obtained using a portable ultrasound machine.

3. The system of aspect 1 or 2, wherein analyzing the pixels in the sonograph comprises:
    identifying right upper quadrant, the left upper quadrant and/or the suprapubic view in the sonogram.

4. The system of any one of the preceding aspects, wherein the software instructions are obtained by training a sonogram analysis system to analyze pixels of a sonogram using pre-annotated abdominal sonograms wherein the pixels are labeled as corresponding to anatomic structures and if present, to free fluid.

5. The system of aspect 3 or 4, wherein the pre-annotated abdominal sonograms comprise pixel level annotation to delineate bladder, kidney, liver, spleen, and/or free fluid.

6. The system of any one of aspects 3-5, wherein the pre-annotated abdominal sonograms are annotated by a radiologist or clinical expert.

7. The system of any one of aspects 3-6, wherein the pre-annotated abdominal sonograms comprise at least about 100 sonograms.

8. The system of any one of aspects 3-6, wherein the pre-annotated abdominal sonograms comprise at least about 500 sonograms.

9. The system of any one of aspects 3-8, wherein the training comprises up to 25 repetitions with each of the pre-annotated sonogram.

10. The system of any one of aspects 3-8, wherein the training comprises up to 50 repetitions with each of the pre-annotated sonogram.

11. The system of any one of aspects 3-10, wherein the training is performed on a UNET CNN algorithm.

12. The system of any one of aspects 3-11, wherein the training comprises stochastic gradient descent with restarts (SGDR).

13. The system of any one of aspects 1-12, wherein the system identifies abdominal free fluid and anatomic structures with a 71-98% accuracy.

14. The system of any one of aspects 1-13, wherein the system comprises a non-transitory processor-readable storage medium that stores the processor-executable software instructions.

15. A non-transitory processor-readable storage medium that stores the processor-executable software instructions according to any one of aspects 1-14.

16. A machine-learning system, comprising:
a non-transitory processor-readable storage medium that stores a processor-executable instruction; and
a processor communicably coupled to the non-transitory processor-readable storage medium, the processor:
receives learning data comprising a plurality of unannotated sonograms and annotated versions thereof, each sonogram comprising pixels representative of an anatomical structure and of free fluid, if present, and each annotated sonogram comprising identification of an anatomical structure depicted by the pixels and of free fluid, if present;
trains a convolutional neural network (CNN) model to segment anatomical structures and free fluid, if present, utilizing the received learning data; and
stores the trained CNN model in the non-transitory processor-readable storage medium of the machine learning system,
wherein the sonograms are sonograms of abdomen of patients.

17. The machine-learning system of aspect 16, wherein the unannotated sonogram and the annotated version thereof are in a single image comprising pixels and metadata associated with the pixels, wherein the metadata comprises the annotation regarding pixels representative of an anatomical structure and of free fluid, if present.

18. The machine-learning system of aspect 17, wherein the metadata comprising annotation regarding pixels representative of an anatomical structure and of free fluid, if present, comprises drawings of anatomical structures and of free fluid, if present, and a label identifying each of the drawings as a particular anatomical structure and free fluid.

19. The machine-learning system of any one of aspects 16-18, wherein the annotated sonograms are produced by a radiologist.

20. The machine-learning system of any one of aspects 16-19, wherein at least 10% of the sonograms comprise sonograms of patients with free fluid in the abdomen.

21. The machine-learning system of any one of aspects 16-19, wherein at least 30% of the sonograms comprise sonograms of patients with free fluid in the abdomen.

22. The machine-learning system of any one of aspects 16-21, wherein the processor trains a UNET CNN algorithm.

23. The machine-learning system of any one of aspects 16-22, wherein the processor trains the CNN using stochastic gradient descent with restarts (SGDR).

24. The machine-learning system of any one of aspects 16-23, wherein the sonograms comprise views of right upper quadrant, RUQ, left upper quadrant, LUQ, and/or suprapubic, SP views.

25. A non-transitory processor-readable storage medium that stores the processor-executable software instructions according to any one of aspects 16-24.

26. A computer-implemented method for analyzing a sonogram of a patient's abdomen to automatically identify anatomical structures and determine presence or absence of free fluid in the patient's abdomen, the method comprising:
analyzing pixels in the sonogram as representing an anatomical structure,
producing a drawing of the anatomical structure based on the analyzing of the pixels; and
if present, a drawing of free fluid in the patient's abdomen; and
outputting:
an image showing the drawing of the anatomical structure and, if present, the free fluid, and/or
an indication of presence or absence of free fluid.

27. The method of aspect 26, wherein the sonogram is a low-resolution sonogram obtained using a portable ultrasound machine.

28. The method of aspect 26 or 27, wherein analyzing the pixels in the sonograph comprises:
identifying right upper quadrant, the left upper quadrant and/or the suprapubic view in the sonogram.

29. The method of any one of aspects 26-28, wherein the software instructions are obtained by training a sonogram analysis system to analyze pixels of a sonogram using pre-annotated abdominal sonograms wherein the pixels are labeled as corresponding to anatomic structures and if present, to free fluid.

30. The method of aspect 29, wherein the pre-annotated abdominal sonograms comprise pixel level annotation to delineate bladder, kidney, liver, spleen, and/or free fluid.

31. The method of aspect 29 or 30, wherein the pre-annotated abdominal sonograms are annotated by a radiologist.

32. The method of any one of aspects 29-31, wherein the pre-annotated abdominal sonograms comprise at least about 100 sonograms.

33. The method of any one of aspects 29-31, wherein the pre-annotated abdominal sonograms comprise at least about 500 sonograms.

34. The method of any one of aspects 29-33, wherein the training comprises up to 25 repetitions with each of the pre-annotated sonogram.

35. The method of any one of aspects 29-33, wherein the training comprises up to 50 repetitions with each of the pre-annotated sonogram.

36. The method of any one of aspects 29-35, wherein the training is performed on a UNET CNN algorithm.

37. The method of any one of aspects 29-36, wherein the training comprises stochastic gradient descent with restarts (SGDR).

38. The method of any one of aspects 26-37, wherein the method identifies abdominal free fluid and anatomic structures with a 71-98% accuracy.

39. A method for training a convolutional neural network (CNN) model, the method comprising:
providing a non-transitory processor-readable storage medium that stores a processor-executable instruction; and a processor communicably coupled to the non-transitory processor-readable storage medium, using the processor for
receiving learning data comprising a plurality of unannotated sonograms and annotated versions thereof, each sonogram comprising pixels representative of an anatomical structure and of free fluid, if present, and each annotated sonogram comprising identification of an anatomical structure depicted by the pixels and of free fluid, if present;
training a convolutional neural network (CNN) model to segment anatomical structures and free fluid, if present, utilizing the received learning data; and
storing the trained CNN model in the non-transitory processor-readable storage medium of the machine learning system,
wherein the sonograms are sonograms of abdomen of patients.

40. The method of aspect 39, wherein the unannotated sonogram and the annotated version thereof are in a single image comprising pixels and metadata associated with the pixels, wherein the metadata comprises the annotation regarding pixels representative of an anatomical structure and of free fluid, if present.

41. The method of aspect 40, wherein the metadata comprising annotation regarding pixels representative of an anatomical structure and of free fluid, if present, comprises drawings of anatomical structures and of free fluid, if present, and a label identifying each of the drawings as a particular anatomical structure and free fluid.

42. The method of any one of aspects 39-41, wherein the annotated sonograms are generated by a radiologist.

43. The method of any one of aspects 39-42, wherein at least 10% of the sonograms comprise sonograms of patients with free fluid in the abdomen.

44. The method of any one of aspects 39-42, wherein at least 30% of the sonograms comprise sonograms of patients with free fluid in the abdomen.

45. The method of any one of aspects 39-44, wherein the processor trains a UNET CNN algorithm.

46. The method of any one of aspects 39-45, wherein the processor trains the CNN using stochastic gradient descent with restarts (SGDR).

47. The method of any one of aspects 39-46, wherein the sonograms comprise views of right upper quadrant, RUQ, left upper quadrant, LUQ, and/or suprapubic, SP views.

The following examples are offered by way of illustration and not by way of limitation.

EXPERIMENTAL

Using Artificial Intelligence to Improve Reliability of the Focused Assessment with Sonography for Trauma (FAST): A Pilot Study of FAST-AI

SUMMARY

Background: The abdominal FAST examination is a screening test for hemorrhage that if interpreted correctly, can improve patient outcomes. However, it has limitations, including erroneous interpretation secondary to operator error which can lead to unnecessary testing, delays in therapy, increased cost and avoidable invasive procedures. We hypothesized that artificial intelligence (AI) could enhance imaging recognition and reliability on point of care FAST ultrasound.

Methods: 249 highest level trauma activation patients with a complete archived FAST study were identified. The three FAST abdominal views (RUQ, LUQ, Suprapubic) were read by two expert clinicians blinded to the clinical care. Views were dichotomized as positive or negative for free fluid and pixel level annotation of anatomic structures of interest and free fluid was performed. The annotated data was divided into 80% development and 20% validation datasets. A Residual Neural Network (ResNet) was performed to assess Classification (binary outcome of positive or negative free fluid) and Detection (identification of specific anatomic structures). A RetinaNet was utilized to assess Location and a UNET algorithm used to assess Segmentation (pixel level identification of structures).

Results: The ResNet neural network (n=60 patients, 141 images) Classification results were promising with 89.2% accuracy after 125 epochs (repetitions) for determination of free fluid presence or absence. Detection of anatomic structures was variable in performance with the best identification of the suprapubic view, but worse performance for free fluid (40% accuracy). Localization performed similarly to Detection. Most promisingly, Segmentation (n=249 patients, 576 images) was able to identify free fluid and anatomic structures with a DICE evaluation metric (reproducibility validation metric) of 0.71 to 0.98 or 71-98% accuracy.

Materials and Methods

Study Design and Setting

This is a retrospective pilot study using a hospital trauma registry and Picture Archiving and Communication System (PACS) to develop and validate a machine learning computer-aided model to interpret FAST examinations in patients with blunt injury. This is a single center study conducted at an urban Level 1 trauma center. The trauma registry was queried from 2012-2016, for patients 18 years of age or older that met the hospital's highest trauma activation criteria and had an adequate abdominal FAST examination recorded in the hospital's PACS archiving system. FAST examinations are completed by credentialed board-certified emergency medicine and trauma faculty. FAST examinations undergo regular quality assurance review. The adequacy of the abdominal FAST examinations were determined by two independent expert reviewers for the presence of all three views (right upper quadrant, RUQ, left upper quadrant, LUQ, and suprapubic, SP views) and adequate quality of images (landmarks, gain, depth). The study was approved by the Institutional Review Boards of the institutions.

Data Sets

From the identified 860 patients with at least one archived ultrasound FAST image, 249 had adequate images for all abdominal views of the FAST in Dicom format. All images were de-identified per the Health Insurance Portability and Accountability Act Safe Harbor prior to review. The three FAST abdominal views were read by two clinicians with expertise in the FAST examination and blinded to the clinical care.

Annotation

Each FAST examination clip was subsequently fragmented into still images. Representative still images were further dichotomized as positive or negative for free fluid and pixel level annotation was performed by the clinicians to delineate structures of interest including bladder, kidney, liver, spleen, and free fluid using an annotation platform adapted for medical imaging (FIG. 1).

Development of the Algorithm

Four candidate deep learning approaches were assessed. The first was Classification. Classification assesses the binary outcome of whether or not hemoperitoneum is present. Detection is an approach where the presence of specific anatomic structures in an image is identified by the algorithm. The third method tested was a Localization strategy which results with rectangular bounding boxes being superimposed over structures of interest in the images. Finally, a Segmentation strategy was assessed, which identifies anatomic structures at the pixel level.

For the classification approach, a subset of the data (n=60 patients, 141 images) were split randomly into an 80% training and 20% validation groups. The dataset was weighted to have 60% negative images (no hemoperitoneum) and 40% positives. A pretrained ResNet101 convolutional neural network was employed. Learning rate is a hyperparameter which is responsible for speeding convergence while simultaneously avoiding being stuck in a local minima on the error surface. A 'stochastic gradient descent with restarts' (SGDR) implementation was used. SGDR forces the model to jump to a different part of the error surface after each epoch of training, by temporarily increasing the learning rate. Thus, the algorithm can exit local minima if it appears to be stuck. To allow for more reliable outcomes when testing the model's classifications, 'test time augmentation' (TTA) was used. TTA involves creating 4 slightly transformed versions of an image employed for testing, and along with the unaltered image, we evaluate the model's performance on all 5 images. The average of these 5 scores is used as the final metric for determining which class the test image belongs to.

For the Detection approach, a pretrained ResNet34 algorithm was utilized with the full dataset (n=249 patients, 576 images) and 80% training and 20% validation split. A 'cyclical learning rate' (CLR) was employed. With CLR, the learning rate is cycled between a predetermined lower and upper bound. This can allow for similar benefits to SGDR, yet is computationally cheaper. Differential learning rates were also applied. This means that different learning rates were assigned on different parts of the network during training. This is an effective strategy due to the fact that the weights in a network are not all fitted at the same speed. To allow for more conservative performance with less false positives, the decision threshold was set at 0.7.

A RetinaNet151 was utilized to assess Localization with the 80% and 20% split as in the prior approaches with 281 images. RetinaNet works in part by creating rectangular boxes and applying them to an image, then determining if an object lies within any of those boxes. Since many more boxes are created than necessary, 'non-maximum suppression' (NMS) was used. This means boxes with a probability of less than 0.45 of an object present, were discarded, Data augmentation without cropping of the images was used. Fifty epochs were performed. CLR with the Adam optimizer were employed. Adam ("Adaptive Moment Estimation") is an extension of SGD, which stores both an exponentially decaying average of past gradients and past squared gradients, which results in better performance.

Finally, a UNET algorithm was used to implement a Segmentation approach. The full dataset (n=249 patients, 576 images) was split 80% training and 20% validation split with the 60% negative and 40% positive class balance. The input data were pixel level annotation and slice pairs. SGDR with a differential learning rate was employed. A Dice metric was reported to evaluate the performance of the model. This metric measures the similarity between the automated detection of the region of interest, and the object in the ground truth annotated image. A Dice score reflects the number of true positives and penalizes for the number of false positives. It is represented by the formula:

$$Dice = \frac{2*TP}{2*TP + FP + FN}$$

Where TP stands for true positive, FP is false positive, and FN is false negative.

Results

Figure 2:
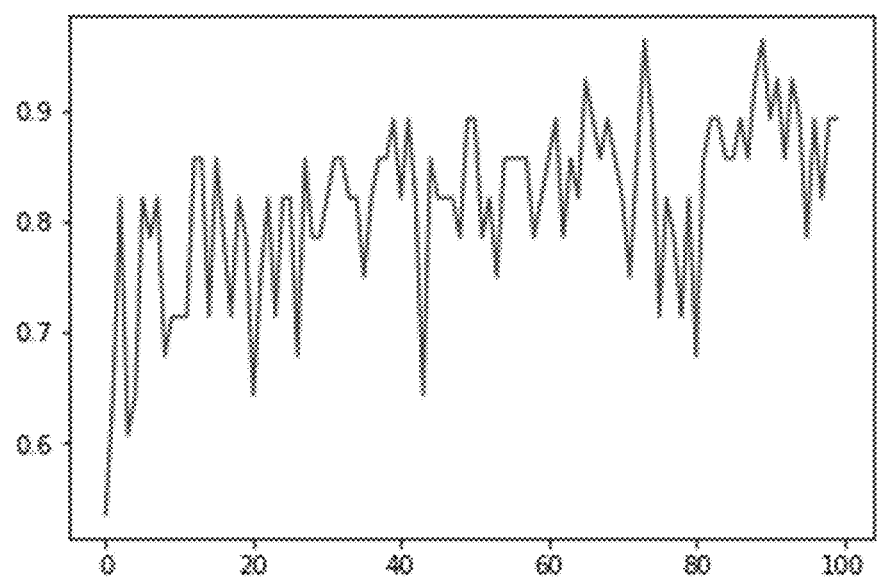
FIG. 2. Classification Accuracy Results with first 100 epochs. Legend: x-axis is number of Epochs; y-axis is accuracy.
Figure 3:
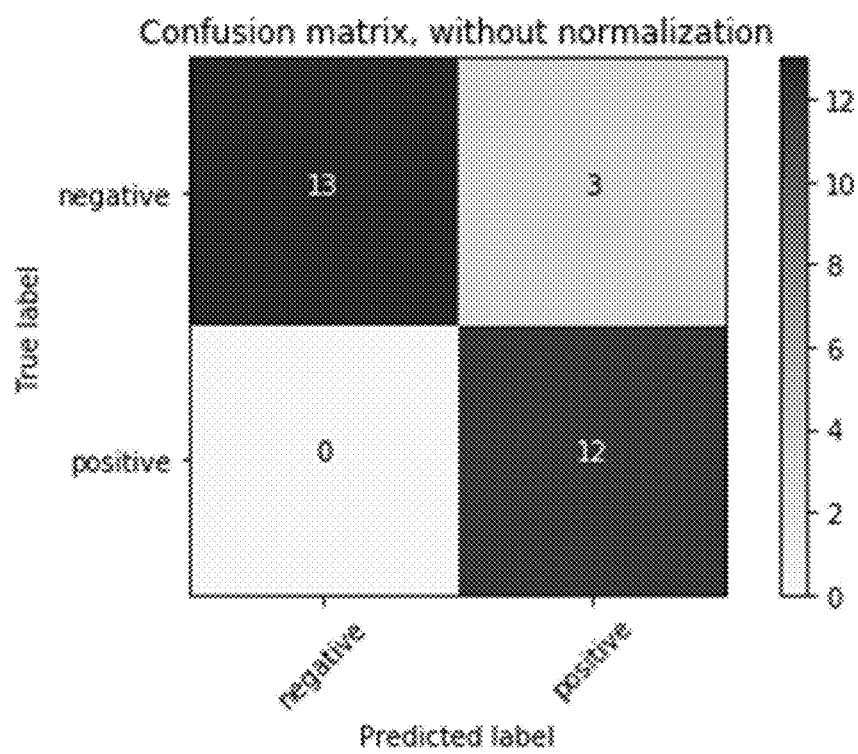
FIG. 3. Validation confusion matrix for validation dataset for Classification approach.

The total dataset included 249 patients, 576 annotated images, meeting inclusion criteria. The ResNet neural network (n=60 patients, 141 images) Classification results were promising with 89.2% accuracy after 125 epochs (repetitions) for determination of the presence or absence of free fluid (FIG. 2). The accuracy of the training dataset converges (reaches the optimal solution) after about 100 epochs and does not change when increased to 125 epochs. confusion matrix reveals in the validation data, there was no false negatives and 3 false positives resulting in a sensitivity of 100% and specificity of 81% (FIG. 3).

Figure 4:
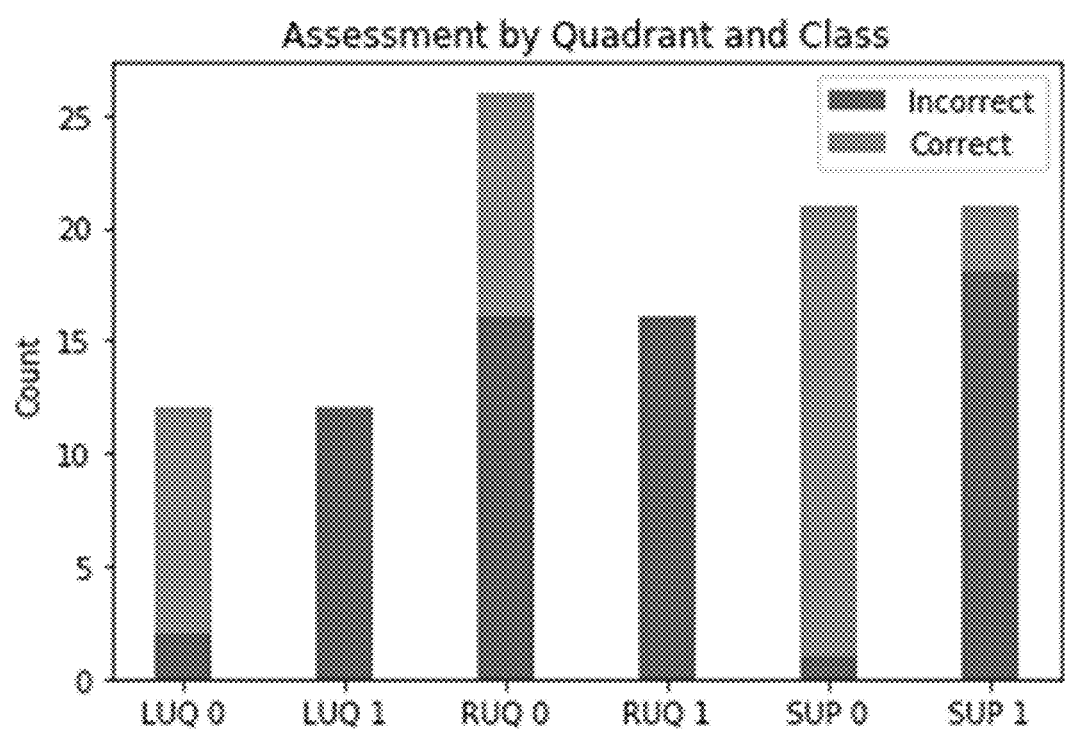
FIG. 4. Free Fluid Detection Results of Each Quadrant by Class. Legend: LUQ: left upper quadrant, RUQ: right upper quadrant; SUP: suprapubic; Class 0: no free fluid; Class 1: free fluid present.

In contrast, Detection of anatomic structures using ResNet was variable in performance with the most accurate detection of the model being the suprapubic view when compared to the RUQ and LUQ view. The worst performance for the Detection model was for the recognition of free fluid (FIG. 4). Overall, accuracy for recognition of free fluid was only 39.9% for the studies when considering the results of all abdominal FAST examination views. Localization results were similar with overall accuracy for recognition of free fluid being 30%.

Figure 5:
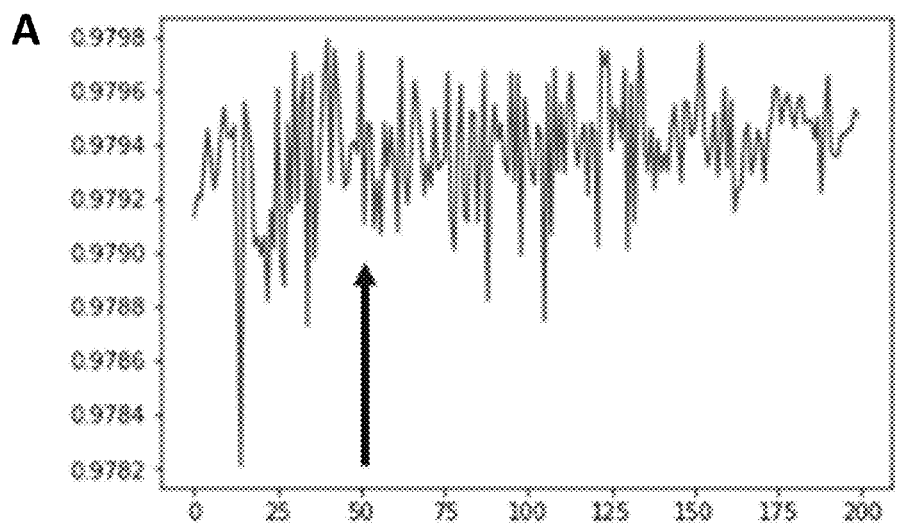
FIG. 5. Training set accuracy and resulting images.
Figure 5:
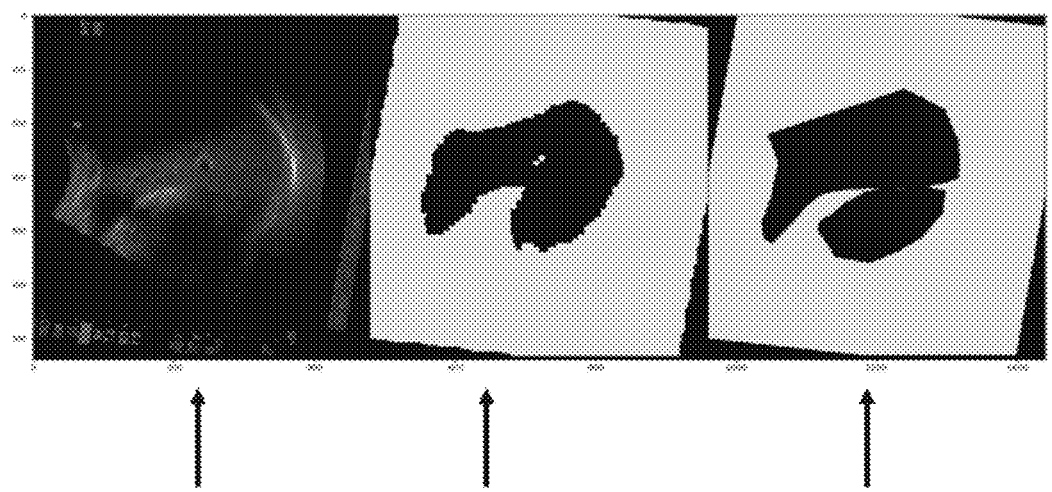
Figure 6:
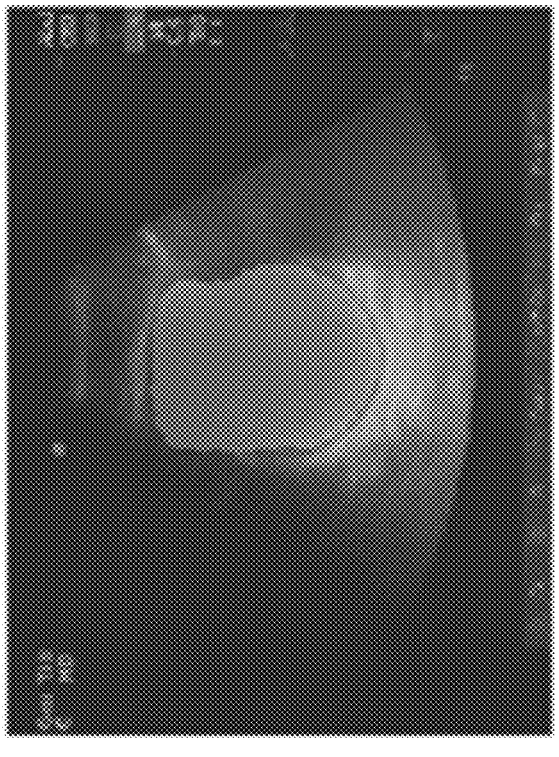
FIG. 6. Suprapubic view FAST image with pixel level annotation by a clinician and artificial intelligence (AI) generated image.
Figure 6:
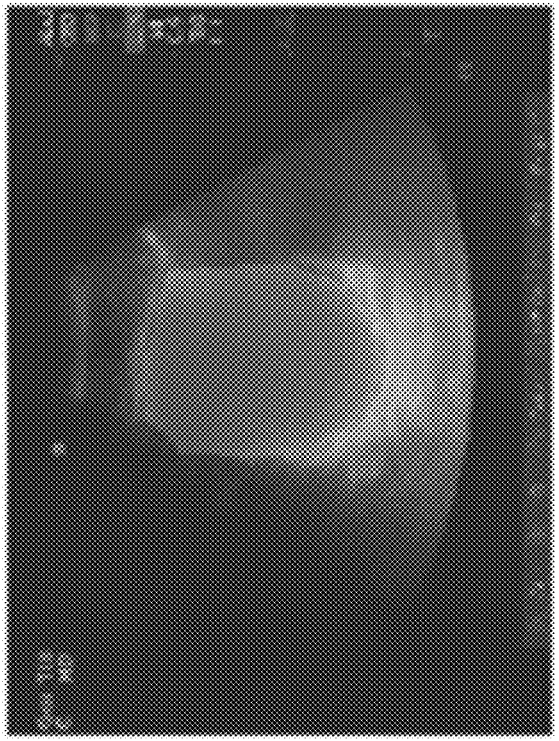

Lastly, Segmentation (n=249 patients, 576 images) identified abdominal free fluid and anatomic structures with a Dice evaluation metric (reproducibility validation metric) of 0.71-98% accuracy (FIG. 5A—accuracy after 50 epochs; 5B—identification of structures).

REFERENCES

1. Mock C, Quansah R, Krishnan R, Arreola-Risa C, Rivara F. Strengthening the prevention and care of injuries worldwide. Lancet. 2004; 363(9427):2172-9.
2. Krug E G, Sharma G K, Lozano R. The global burden of injuries. Am J Public Health. 2000; 90(4):523-6.
3. Callcut R A, Kornblith L Z, Conroy A S, Robles A J, Meizoso J P, Namias N, Meyer D E, Haymaker A, Truitt M S, Agrawal V, et al. The why and how our trauma patients die: A prospective Multicenter Western Trauma Association study. J Trauma Acute Care Surg. 2019; 86(5):864-70.
4. Melniker L A, Leibner E, McKenney M G, Lopez P, Briggs W M, Mancuso C A. Randomized controlled clinical trial of point-of-care, limited ultrasonography for trauma in the emergency department: the first sonography outcomes assessment program trial. Ann Emerg Med. 2006; 48(3):227-35.

5. McKenney M, Lentz K, Nunez D, Sosa J L, Sleeman D, Axelrad A, Martin L, Kirton O, Oldham C. Can ultrasound replace diagnostic peritoneal lavage in the assessment of blunt trauma? J Trauma. 1994; 37(3):439-41.
6. Stengel D, Leisterer J, Ferrada P, Ekkernkamp A, Mutze S, Hoenning A. Point-of-care ultrasonography for diagnosing thoracoabdominal injuries in patients with blunt trauma. Cochrane Database Syst Rev. 2018; 12:CD012669.
7. Savatmongkorngul S, Wongwaisayawan S, Kaewlai R. Focused assessment with sonography for trauma: current perspectives. Open Access Emerg Med. 2017; 9:57-62.
8. Rozycki G S, Ochsner M G, Schmidt J A, Frankel H L, Davis T P, Wang D, Champion H R. A prospective study of surgeon-performed ultrasound as the primary adjuvant modality for injured patient assessment. J Trauma. 1995; 39(3):492-8; discussion 8-500.
9. Sato M, Yoshii H. Reevaluation of ultrasonography for solid-organ injury in blunt abdominal trauma. Journal of ultrasound in medicine: official journal of the American Institute of Ultrasound in Medicine. 2004; 23(12):1583-96.
10. Jang T, Kryder G, Sineff S, Naunheim R, Aubin C, Kaji A H. The technical errors of physicians learning to perform focused assessment with sonography in trauma. Acad Emerg Med. 2012; 19(1):98-101.
11. Damewood S, Jeanmonod D, Cadigan B. Comparison of a multimedia simulator to a human model for teaching FAST exam image interpretation and image acquisition. Acad Emerg Med. 2011; 18(4):413-9.
12. Thomas B, Falcone R E, Vasquez D, Santanello S, Townsend M, Hockenberry S, Innes J, Wanamaker S. Ultrasound evaluation of blunt abdominal trauma: program implementation, initial experience, and learning curve. J Trauma. 1997; 42(3):384-8; discussion 8-90.
13. Richards J R, McGahan J P. Focused Assessment with Sonography in Trauma (FAST) in 2017: What Radiologists Can Learn. Radiology. 2017; 283(1):30-48.
14. Brattain L J, Telfer B A, Dhyani M, Grajo J R, Samir A E. Machine learning for medical ultrasound: status, methods, and future opportunities. Abdom Radiol. 2018; 43(4): 786-99.
15. Sjogren A R, Leo M M, Feldman J, Gwin J T. Image Segmentation and Machine Learning for Detection of Abdominal Free Fluid in Focused Assessment With Sonography for Trauma Examinations: A Pilot Study. J Ultrasound Med. 2016; 35(11):2501-9.
16. Blehar D J, Barton B, Gaspari R J. Learning curves in emergency ultrasound education. Acad Emerg Med. 2015; 22(5):574-82.
17. Becker A, Lin G, McKenney M G, Marttos A, Schulman C I. Is the FAST exam reliable in severely injured patients? Injury. 2010; 41(5):479-83.
18. Sierzenski P R, Schofer J M, Bauman M J, Nomura J T. The double-line sign: a false positive finding on the Focused Assessment with Sonography for Trauma (FAST) examination. J Emerg Med. 2011; 40(2):188-9.
19. Bentley S, Mudan G, Strother C, Wong N. Are Live Ultrasound Models Replaceable? Traditional versus Simulated Education Module for FAST Exam. West J Emerg Med. 2015; 16(6):818-22.
20. Steinemann S, Fernandez M. Variation in training and use of the focused assessment with sonography in trauma (FAST). Am J Surg. 2018; 215(2):255-8.

Accordingly, the preceding merely illustrates the principles of the present disclosure. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A system for analyzing a sonogram of a patient's abdomen to automatically identify anatomical structures and determine presence or absence of free fluid in the patient's abdomen, the system comprising:
    (i) software instructions;
    (ii) a processor configured to execute the instructions for:
        analyzing pixels in the sonogram as representing an anatomical structure, wherein analyzing pixels in the sonogram comprises:
        utilizing a first machine learning algorithm to classify the sonogram as a) including free fluid or b) not including free fluid; and
        utilizing a second machine learning algorithm to segment the sonogram by producing a drawing of the anatomical structure based on the analyzing of the pixels; and
        if present, drawing of free fluid in the patient's abdomen; and
    (iii) an output configured for providing:
        an image showing the drawing of the anatomical structure and, if present, the free fluid, and/or
        an indication presence or absence of free fluid in the patient's abdomen.

2. The system of claim 1, wherein the sonogram is a low-resolution sonogram obtained using a portable ultrasound machine.

3. The system of claim 1, wherein analyzing the pixels in the sonogram comprises:
    identifying right upper quadrant, the left upper quadrant and/or the suprapubic view in the sonogram.

4. The system of claim 3, wherein the pre-annotated abdominal sonograms comprise pixel level annotation to delineate bladder, kidney, liver, spleen, and/or free fluid.

5. The system of claim 3, wherein the pre-annotated abdominal sonograms are annotated by a radiologist or clinical expert.

6. The system of claim 3, wherein the pre-annotated abdominal sonograms comprise at least about 100 sonograms.

7. The system of claim 3, wherein the pre-annotated abdominal sonograms comprise at least about 500 sonograms.

8. The system of claim 1, wherein the software instructions are obtained by training a sonogram analysis system to analyze pixels of a sonogram using pre-annotated abdominal sonograms wherein the pixels are labeled as corresponding to anatomic structures and if present, to free fluid.

9. The system of claim 8, wherein the training comprises up to 25 repetitions with each of the pre-annotated sonogram.

10. The system of claim 8, wherein the training comprises up to 50 repetitions with each of the pre-annotated sonogram.

11. The system of claim 8, wherein the first machine learning algorithm a UNET CNN algorithm.

12. The system of claim 8, wherein the training comprises stochastic gradient descent with restarts (SGDR).

13. The system of claim 1, wherein the system identifies abdominal free fluid and anatomic structures with a 71-98% accuracy.

14. The system of claim 1, wherein the system comprises a non-transitory processor-readable storage medium that stores the processor-executable software instructions.

15. A machine-learning system, comprising:
a non-transitory processor-readable storage medium that stores a processor-executable instruction; and
a processor communicably coupled to the non-transitory processor-readable storage medium,
wherein the processor:
receives learning data comprising a plurality of unannotated sonograms and annotated versions thereof, wherein each sonogram comprising pixels representative of an anatomical structure and of free fluid, if present, and each annotated sonogram comprising identification of an anatomical structure depicted by the pixels and of free fluid, if present;
trains a first convolutional neural network (CNN) model to segment anatomical structures and free fluid, if present, utilizing the received learning data; and, wherein training the first CNN comprises utilizing stochastic gradient descent with restarts (SGDR) and a differential learning rate;
trains a second CNN model to classify sonograms based on a) presence of free fluid and b) absence of free fluid, wherein training the second CNN comprises utilizing SGDR and a differential learning rate; and
stores the first trained CNN model and the second trained CNN model in the non-transitory processor-readable storage medium of the machine learning system,
wherein the sonograms are sonograms of abdomen of patients.

16. The machine-learning system of claim 15, wherein the unannotated sonogram and the annotated version thereof are in a single image comprising pixels and metadata associated with the pixels, wherein the metadata comprises the annotation regarding pixels representative of an anatomical structure and of free fluid, if present.

17. The machine-learning system of claim 16, wherein the metadata comprising annotation regarding pixels representative of an anatomical structure and of free fluid, if present, comprises drawings of anatomical structures and of free fluid, if present, and a label identifying each of the drawings as a particular anatomical structure and free fluid.

18. The machine-learning system of claim 15, wherein the annotated sonograms are produced by a radiologist.

19. The machine-learning system of claim 15, wherein at least 10% of the sonograms comprise sonograms of patients with free fluid in the abdomen.

20. The machine-learning system of claim 15, wherein at least 30% of the sonograms comprise sonograms of patients with free fluid in the abdomen.

21. The machine-learning system of claim 15, wherein the first CNN is a UNET CNN algorithm.

22. The machine-learning system of claim 15, wherein the sonograms comprise views of right upper quadrant, RUQ, left upper quadrant, LUQ, and/or suprapubic, SP views.

23. A method for training a convolutional neural network (CNN) model, the method comprising:
providing a non-transitory processor-readable storage medium that stores a processor-executable instruction; and a processor communicably coupled to the non-transitory processor-readable storage medium; and
using the processor for:
receiving learning data comprising a plurality of unannotated sonograms and annotated versions thereof, wherein each sonogram comprising pixels representative of an anatomical structure and of free fluid, if present, and each annotated sonogram comprising identification of an anatomical structure depicted by the pixels and of free fluid, if present;
training a first convolutional neural network (CNN) model to segment anatomical structures and free fluid, if present, utilizing the received learning data, wherein training the first CNN comprises utilizing stochastic gradient descent with restarts (SGDR) and a differential learning rate;
training a second CNN model to classify sonograms based on a) presence of free fluid and b) absence of free fluid, wherein training the second CNN comprises utilizing SGDR and a differential learning rate; and
storing the first trained CNN model and the second trained CNN model in the non-transitory processor-readable storage medium of the machine learning system,
wherein the sonograms are sonograms of abdomen of patients.

24. The method of claim 23, wherein the unannotated sonogram and the annotated version thereof are in a single image comprising pixels and metadata associated with the pixels, wherein the metadata comprises the annotation regarding pixels representative of an anatomical structure and of free fluid, if present.

25. The method of claim 24, wherein the metadata comprising annotation regarding pixels representative of an anatomical structure and of free fluid, if present, comprises drawings of anatomical structures and of free fluid, if present, and a label identifying each of the drawings as a particular anatomical structure and free fluid.

26. The method of claim 23 wherein the annotated sonograms are generated by a radiologist.

27. The method of claim 23, wherein at least 10% of the sonograms comprise sonograms of patients with free fluid in the abdomen.

28. The method of claim 23, wherein at least 30% of the sonograms comprise sonograms of patients with free fluid in the abdomen.

* * * * *

UNITED STATES PATENT AND TRADEMARK OFFICE
CERTIFICATE OF CORRECTION

| | | |
|---|---|---|
| PATENT NO. | : 12,340,895 B2 | Page 1 of 1 |
| APPLICATION NO. | : 17/641279 | |
| DATED | : June 24, 2025 | |
| INVENTOR(S) | : Rachael Callcut et al. | |

It is certified that error appears in the above-identified patent and that said Letters Patent is hereby corrected as shown below:

In the Specification

In Column 1, Line 12, delete "US2020/051392," and insert -- PCT/US2020/051392, --.

In Column 1, Line 15, after "which" delete "application is".

In the Claims

In Column 21, Line 8, In Claim 11, after "algorithm" insert -- is --.

In Column 21, Line 32, In Claim 15, delete "data; and," and insert -- data, --.

Signed and Sealed this
Sixteenth Day of September, 2025

Coke Morgan Stewart
*Acting Director of the United States Patent and Trademark Office*